US008226590B2

(12) United States Patent
Tucker et al.

(10) Patent No.: US 8,226,590 B2
(45) Date of Patent: Jul. 24, 2012

(54) STRESS RADIOGRAPHY POSITIONER

(75) Inventors: Jon B. Tucker, Presto, PA (US);
Geoffrey A. Huber, Pittsburgh, PA (US); Paul F. Mostowy, Pittsburgh, PA (US)

(73) Assignees: Jon B. Tucker, Presto, PA (US); Fred I. Schwartz, Pittsburgh, PA (US); Melvin E. Solomon, Pittsburgh, PA (US)

( * ) Notice: Subject to any disclaimer, the term of this patent is extended or adjusted under 35 U.S.C. 154(b) by 328 days.

(21) Appl. No.: 12/168,300

(22) Filed: Jul. 7, 2008

(65) Prior Publication Data

US 2009/0012437 A1   Jan. 8, 2009

Related U.S. Application Data

(60) Provisional application No. 60/958,611, filed on Jul. 6, 2007.

(51) Int. Cl.
    *A61F 5/00* (2006.01)
(52) U.S. Cl. .......................................... 602/26; 128/845
(58) Field of Classification Search ............... 602/23, 602/26, 27–28; 128/882, 845, 846; 5/647
    See application file for complete search history.

(56) References Cited

U.S. PATENT DOCUMENTS

| 4,069,813 | A |   | 1/1978  | Gilula |
| 4,181,297 | A |   | 1/1980  | Nichols |
| 4,232,681 | A | * | 11/1980 | Tulaszewski ................. 378/208 |
| 4,291,229 | A |   | 9/1981  | Patt |
| 4,320,749 | A |   | 3/1982  | Highley |
| 4,323,080 | A | * | 4/1982  | Melhart ........................ 600/587 |
| 4,592,362 | A |   | 6/1986  | Stedtfeld et al. |
| 4,700,373 | A |   | 10/1987 | Miller |
| 4,827,496 | A |   | 5/1989  | Cheney |
| 5,136,743 | A | * | 8/1992  | Pirela-Cruz ...................... 5/647 |
| 5,228,454 | A |   | 7/1993  | Siegler |
| 5,335,674 | A |   | 8/1994  | Siegler |
| 5,462,068 | A | * | 10/1995 | Rijke et al. ................... 128/881 |
| 5,479,471 | A |   | 12/1995 | Buckland |
| 5,724,991 | A |   | 3/1998  | Rijke et al. |
| 6,419,645 | B1 |  | 7/2002  | Rijke |
| 6,726,642 | B2 |  | 4/2004  | Danielsson et al. |
| 6,773,063 | B2 | * | 8/2004  | Eerkens ........................ 297/248 |

FOREIGN PATENT DOCUMENTS

DE          10123577 A1   12/2002

* cited by examiner

*Primary Examiner* — Michael A. Brown
(74) *Attorney, Agent, or Firm* — The Webb Law Firm (57) ABSTRACT

A knee positioning device for applying stress to a knee joint during a radiographic procedure. The device comprises at least one sectional support board having a plurality of slots therein, a plurality of holding members positioned within the slots, wherein each holding member is configured to support a positioning structure.

10 Claims, 10 Drawing Sheets

STRESS RADIOGRAPHY POSITIONER

CROSS REFERENCE TO RELATED APPLICATIONS

This application claims the benefit of U.S. Provisional Patent Application No. 60/958,611, filed Jul. 6, 2007, which is hereby incorporated by reference.

BACKGROUND OF THE INVENTION

1. Field of the Invention

The present invention relates to devices for applying stress to joints and, more particularly, to a knee stress radiography device used to place stress on a knee joint in a desired position, particularly when an X-ray image of a knee is taken.

2. Description of Related Art

Certain diagnostic X-ray examinations of the knee can be made only when the knee is held in a specific position. In order to accurately perform stress radiography of the knee and other joints, applying stress to the knee is required. This requires a person to hold the patient's leg and apply stress to the knee joint, which causes this person to be in close proximity to the X-ray beam. Further, when the person is holding the patient's leg, the stress applied to the knee at one particular time may not be the same stress applied to the knee at a different time, thereby making it difficult to perform reproducible stress radiography of the knee.

A device for holding a patient's leg for stress radiography has been described in U.S. Pat. No. 4,232,681. This device is a leg positioning device for X-ray filming that has a support with which the leg can be fixedly held at two-spaced locations, a pressure element that can apply incremental variable pressure to the leg intermediate these locations and a device for measuring the applied pressure so that the same can be exactly reproduced whenever desired.

However, this prior art device and others similar to this device are bulky, expensive and do not adjust to fit all body sizes or adjust to apply pressure to the knee at multiple locations and, therefore, may not be used each and every time by a physician. Therefore, it is desirable to provide a stress radiography device that is inexpensive, lightweight, adjustable for all body sizes and positions, and easy to assemble in order for a physician to accurately and reproducibly perform stress radiography of the knee and other joints while remaining safely outside the X-ray beam.

SUMMARY OF THE INVENTION

The present invention provides for a knee positioning device for applying stress to a knee joint during a radiographic procedure. The device comprises at least one sectional support board having a plurality of slots therein, a plurality of holding members positioned within the slots, wherein each holding member is configured to support a positioning structure.

DETAILED DESCRIPTION OF THE INVENTION

An exemplary embodiment of the present invention provides for a device 10 for applying stress to a knee during a radiographic procedure as shown in FIGS. 1-10. The components of the device 10 include at least one sectional support board 12 (preferably two board sections 12A and 12B) having a plurality of spaced apart holes or slots 14 therein, and a plurality of holding members 16 such as pins or pegs adapted to be inserted into the holes 14 in order to support leg positioning structures S (discussed later) that are placed on the assembled support board sections 12A and 12B.

Figure 1:
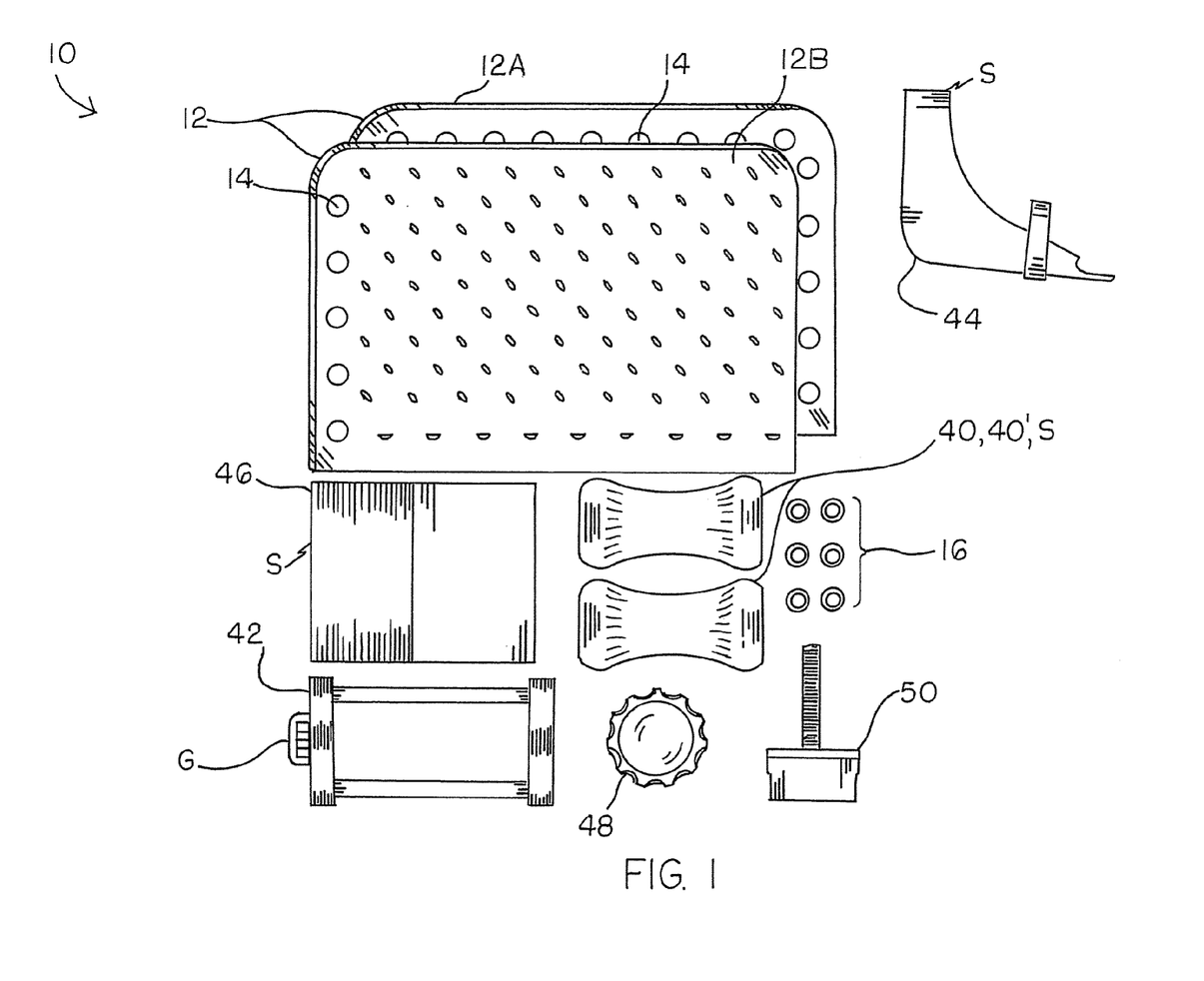
FIG. 1 shows an elevational view of each of the unassembled components of a device according to the present invention.
Figure 2:
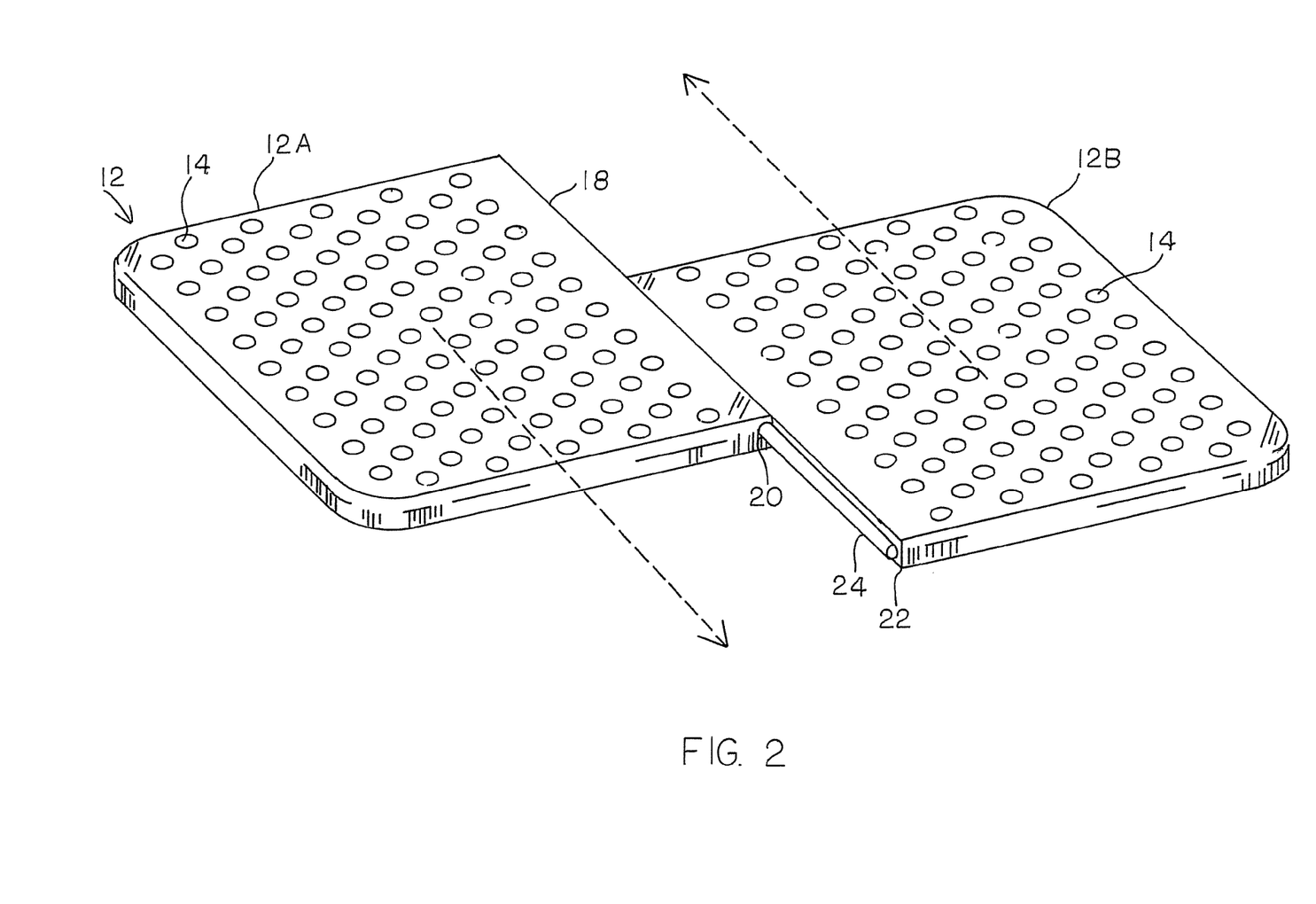
FIG. 2 shows the assembly of the sectional support boards of the device shown in FIG. 1.

Referring to FIG. 2, the board section 12A has one end 18 that includes a semi-circular opening 20 therein and board section 12B has a corresponding end 22 that includes a semi-circular bar or pin 24 that is slidably received within the opening 20 of board end 18 such that board sections 12A and 12B are linearly and releasably attached to each other. The device 10 may also include a plurality of planar sectional boards 12, wherein each board section has both a semi-circular opening 20 on one end and a semi-circular bar 24 on another end (not shown) such that a plurality of board sections may be attached to each other in order to accommodate larger size individuals. For example, the prior art devices are sized to accommodate both the small youth size and the largest adult size, thus making these devices very large and bulky. In contrast, the board sections 12A and 12B of device 10 may be sized to accommodate small to average sized individuals such that the assembled support board 12 is smaller and less bulky than the prior art frame or board. The advantage of device 10 is that additional planar board sections may be added on to accommodate large adult sized persons. Attachment of the support boards 12 to each other may be accomplished by any other manner known in the art such as the use of mechanical fasteners, for example, clamps hinge-pin arrangement or other means such as a snap-fit arrangement. The board sections 12A and 12B may be rectangular shaped and may be made of a lightweight material such as wood, plastic or a lightweight metal.

Figure 3:
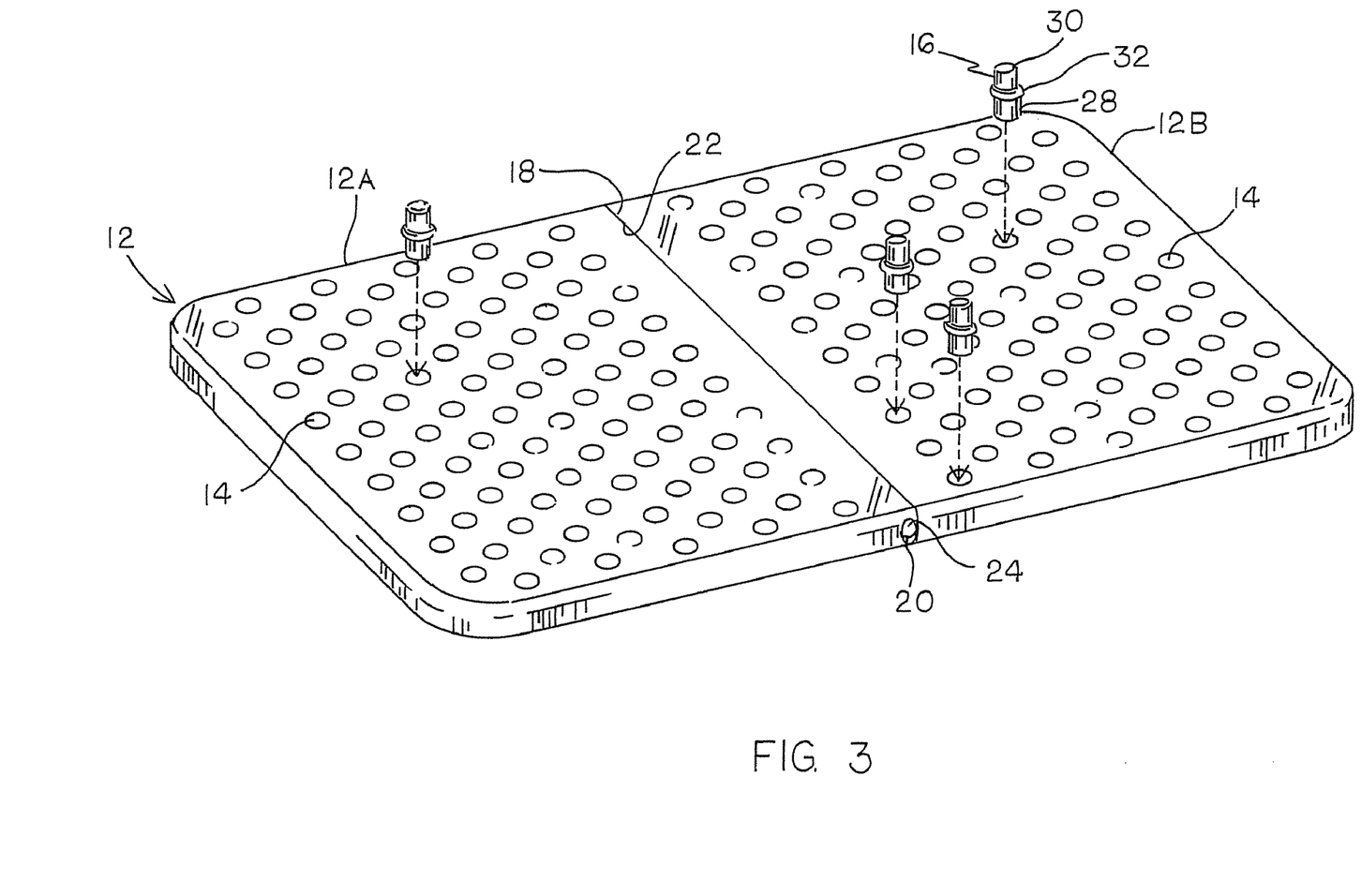
FIG. 3 shows a plurality of holding members being inserted into the slots of the sectional support boards shown in FIG. 2.
Figure 4:
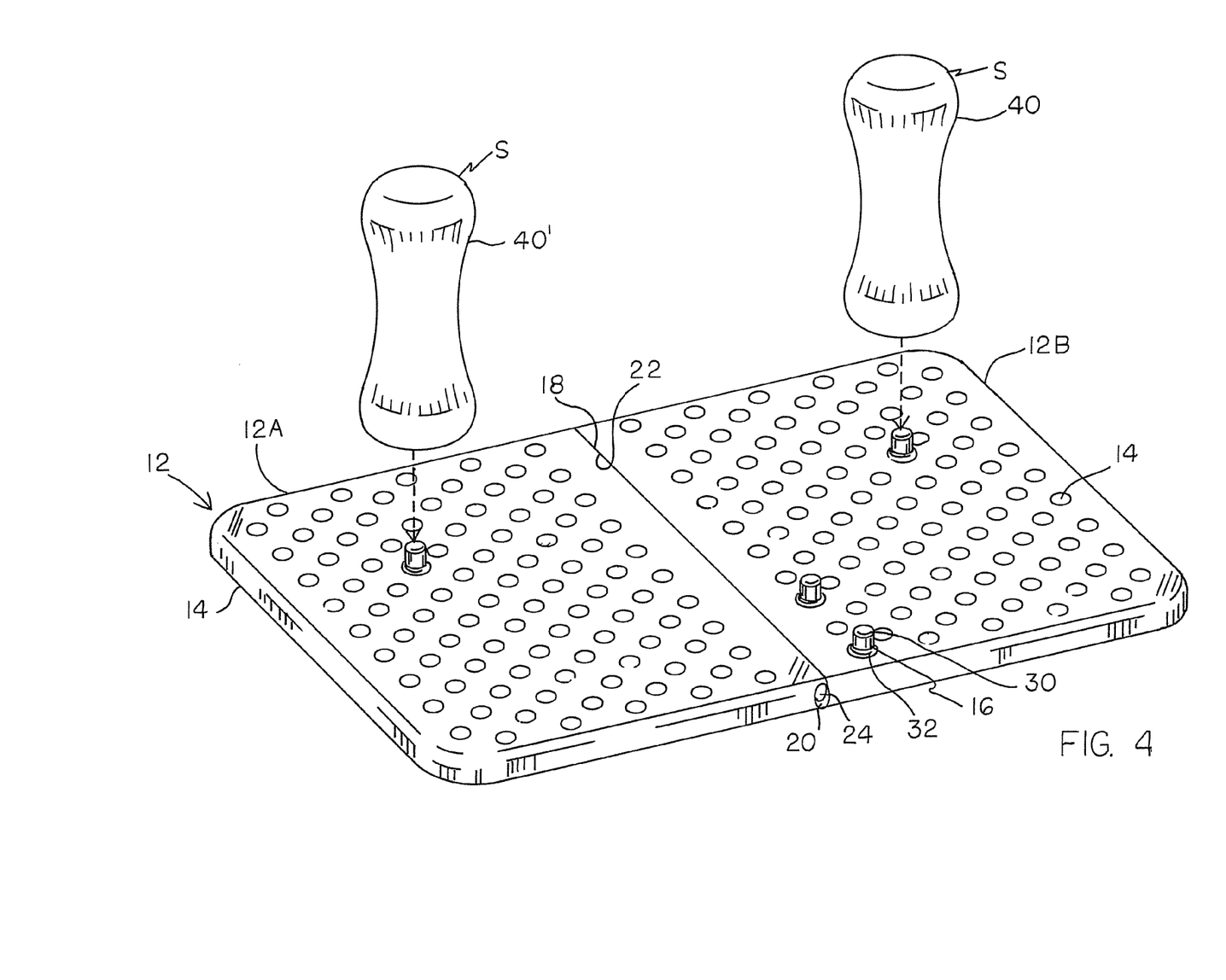
FIG. 4 shows the assembly of support pads being inserted onto the holding members of the device shown in FIG. 3.
Figure 5:
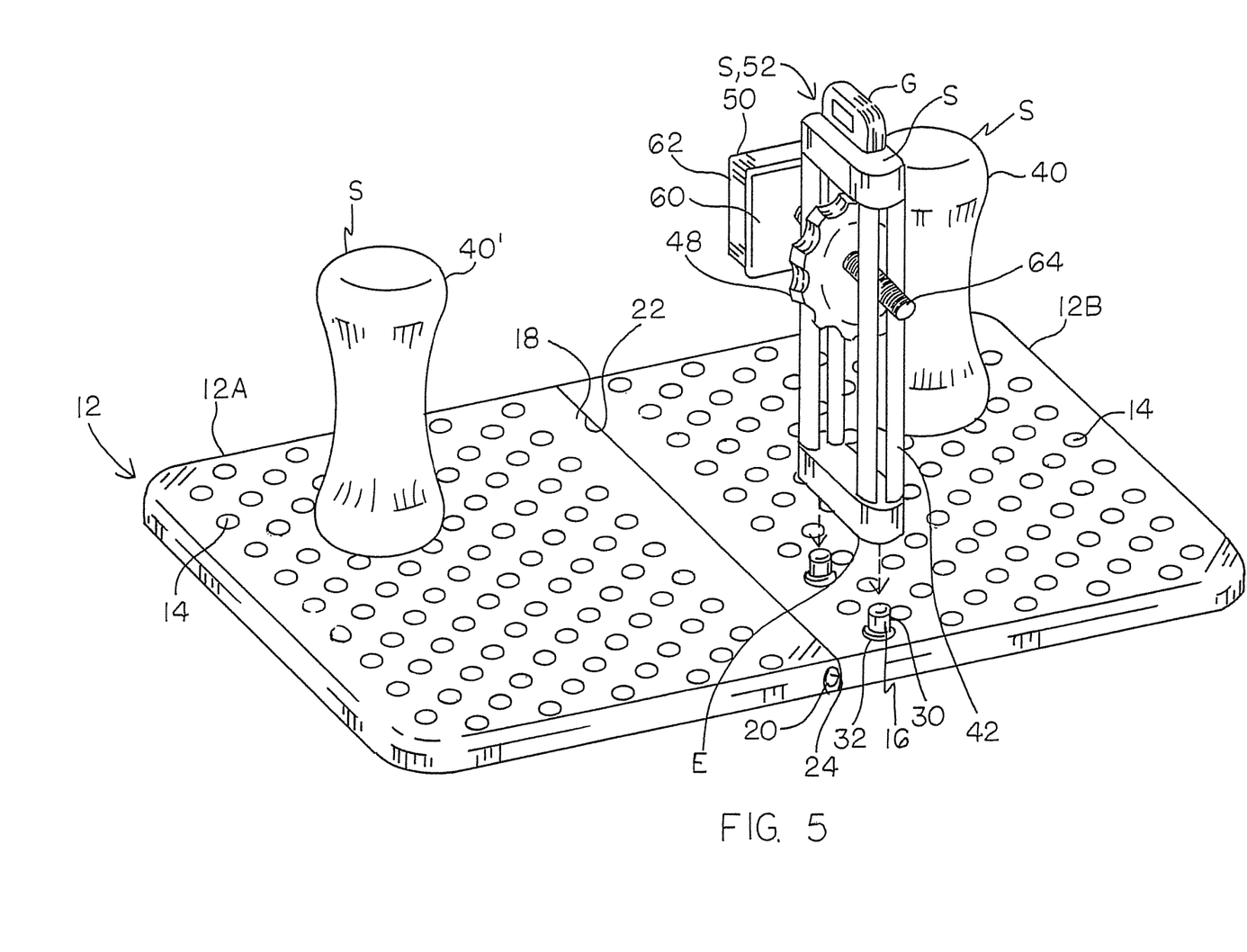
FIG. 5 shows the assembly of a force producing device being inserted onto the holding members of the device shown in FIG. 4.
Figure 6:
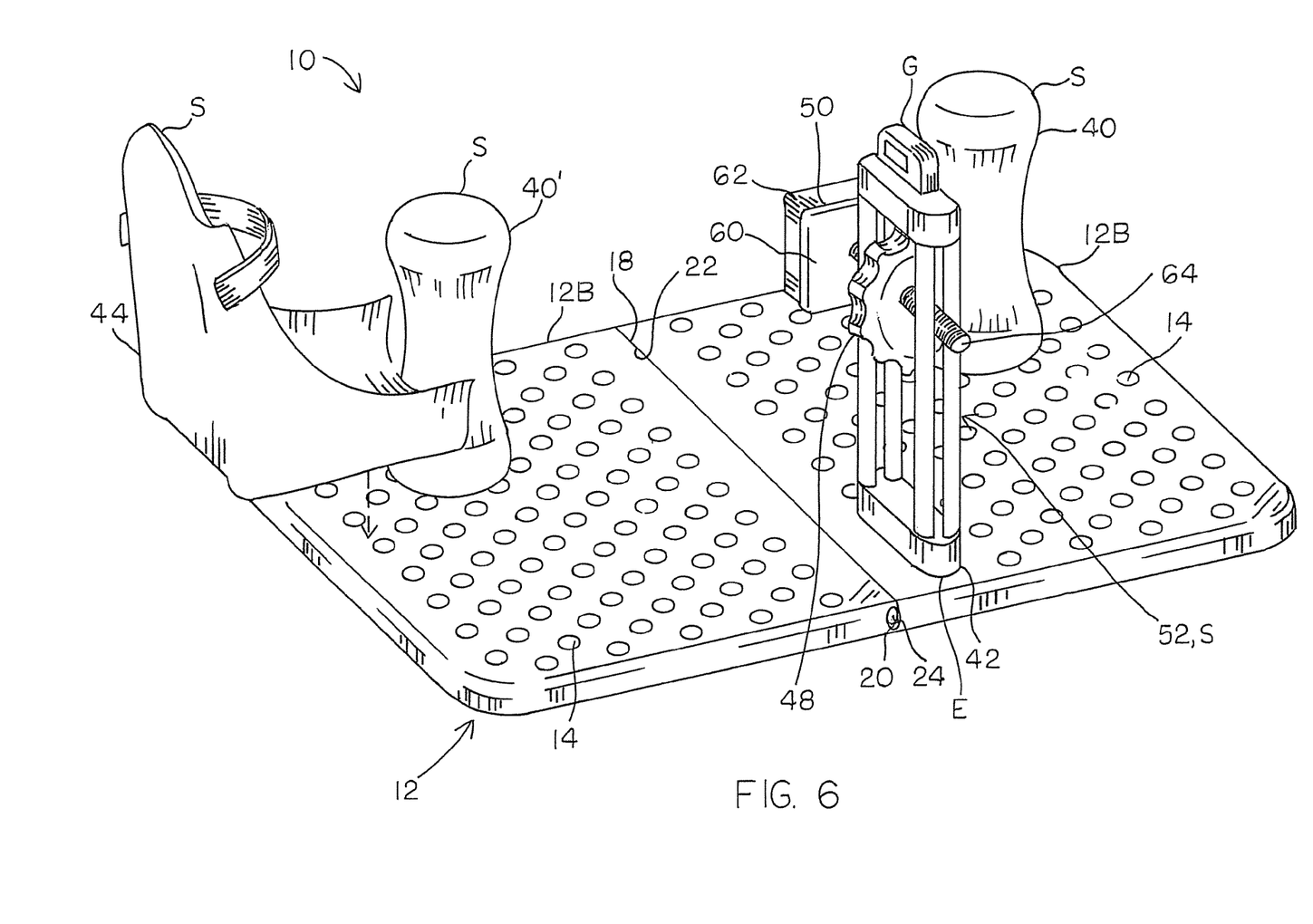
FIG. 6 shows the assembly of a foot support being attached to the support boards of the device shown in FIG. 5.
Figure 7:
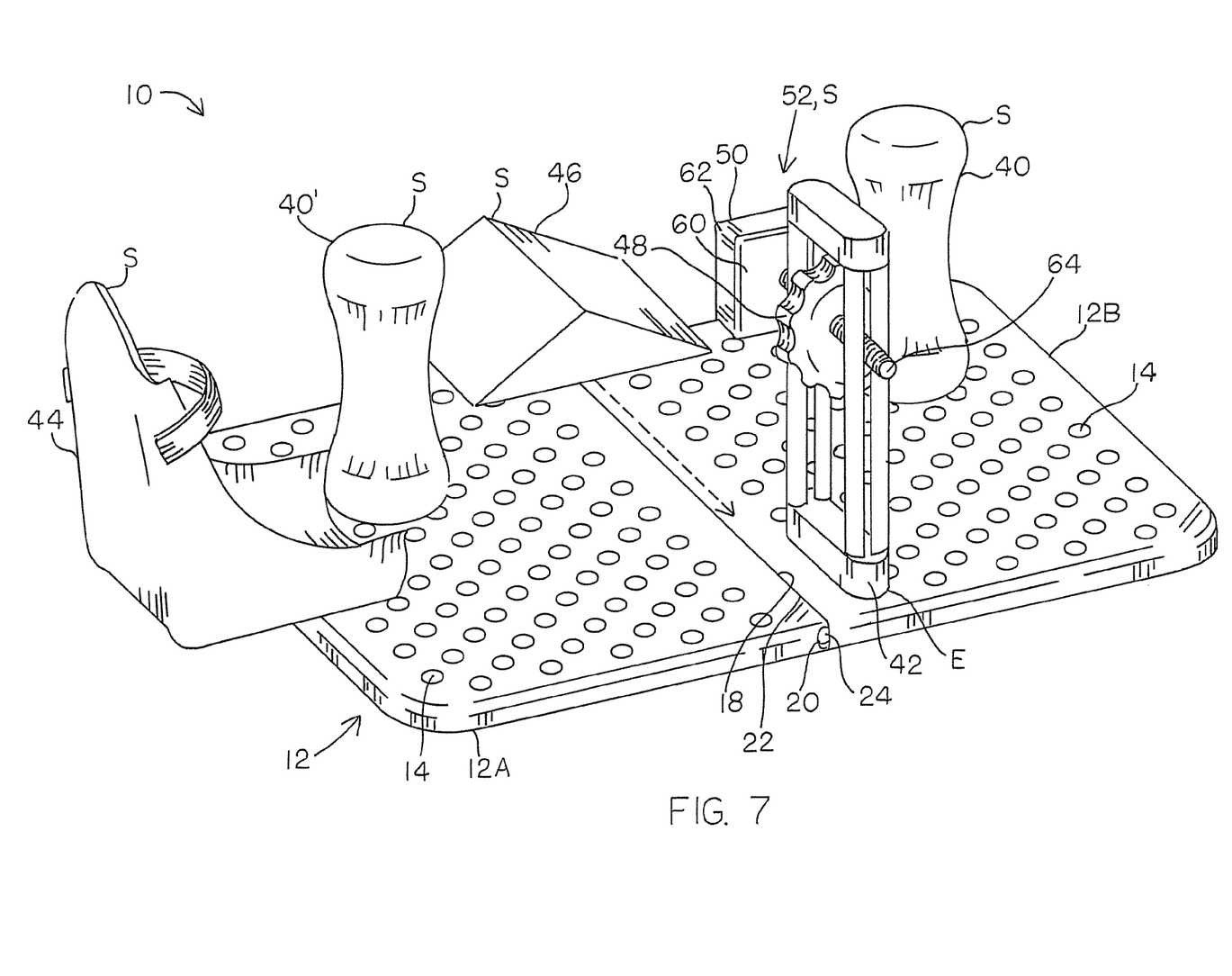
FIG. 7 shows the assembly of an angled knee pad being inserted onto the support boards of the device shown in FIG. 6.
Figure 11:
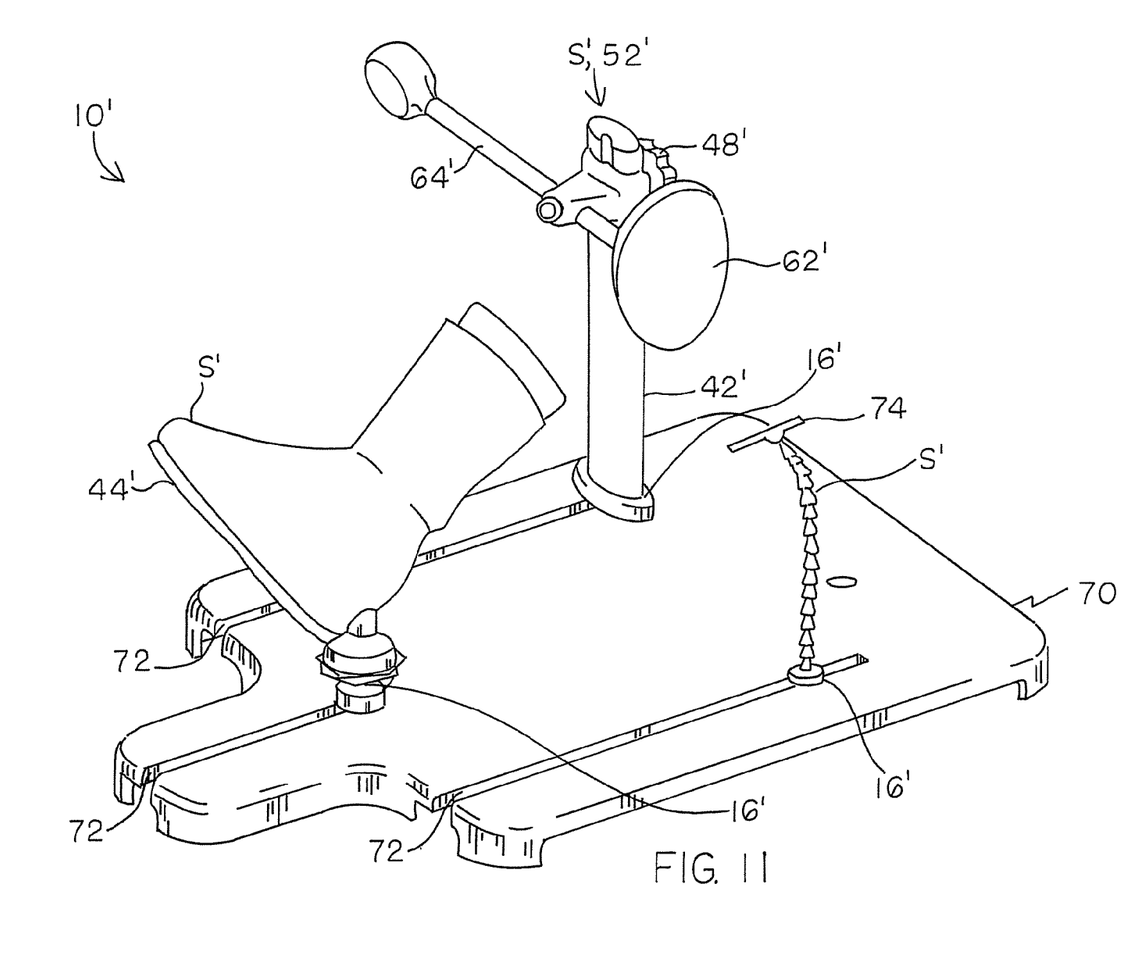
FIG. 11 shows a second embodiment of an assembled knee positioning device of the present invention.

FIG. 3 shows a plurality of holding members 16 inserted into the holes 14 of the support board 12. The holes 14 in the sectional support board 12 may also be elongated slots adapted to receive the holding members 16, wherein the holding members 16 are slidably moved along a longitudinal axis of the slots as shown in FIG. 11. The holding member 16 includes a first section 28, a second section 30 and an annular flange 32 defined therebetween. As shown in FIGS. 3 and 4, the first section 28 is inserted into the holes 14 and the annular flange 32 abuts against the board 12 such that the second section 30 extends upwardly therefrom. The holding members 16 are placed in a desired position for placement of the positioning structures S.

Figure 8:
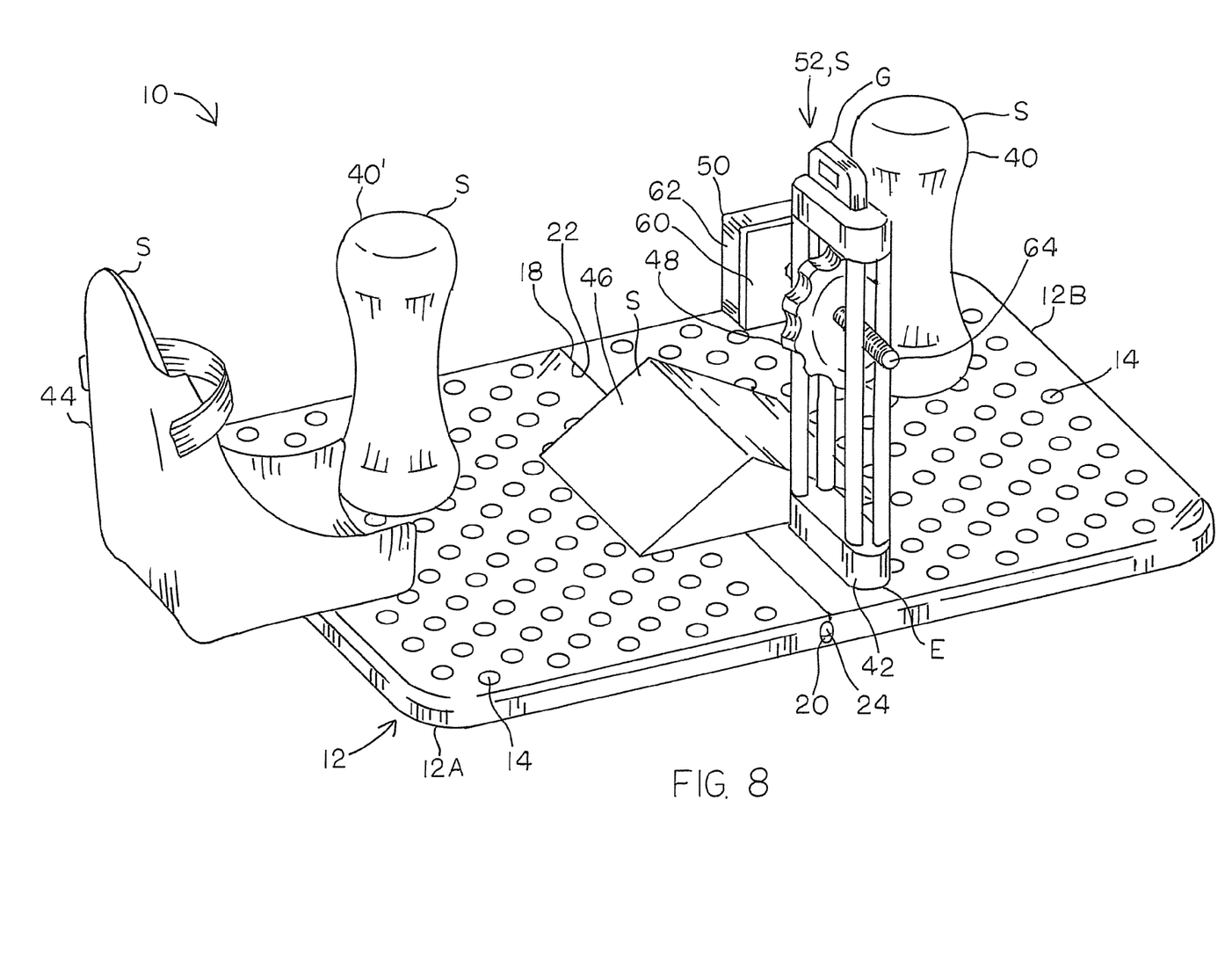
FIG. 8 shows a first embodiment of the assembled knee positioning device shown in FIG. 1.
Figures 9, 10:
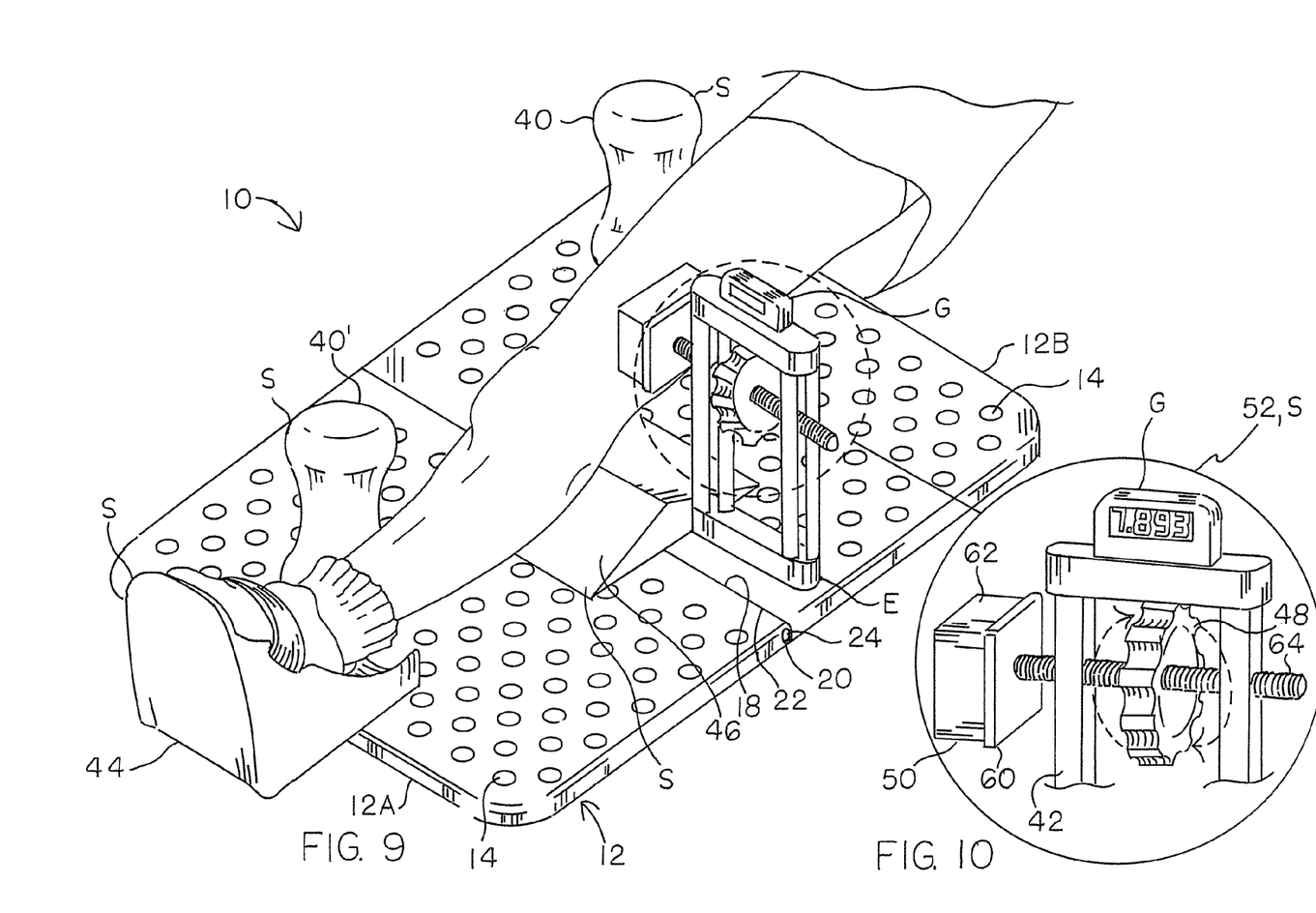
FIG. 9 shows a patient's leg inserted into the device shown in FIG. 8.
FIG. 10 is an exploded view of the force producing device shown in FIG. 9.

Referring to FIGS. 4-10, each of the positioning structures S of the device 10 includes an opening (not shown) for receiving the second section 30 of the holding members 16, thus securing the structure S to the sectional board 12. The positioning structures S may include, but are not limited to, femoral and/or tibial stabilizing pads 40 and 40', which are spaced apart and attached to opposite ends of the sectional board 12 (FIG. 4), a force producing device 52 attached to a side part of the sectional board 12 (FIG. 5), a foot support 44 secured to a front part of the sectional board 12 (FIGS. 6 and 7) and an angled knee pad 46 positioned adjacent the force producing device 52 and attached to a center part of the sectional board 12 (FIG. 8). As shown in FIGS. 5-10, the force producing device 52 may be as simple as a support frame 42 having an end E attached to the support board 12 and a knee pad screw assembly 50 attached to the support frame 42. The assembly 50 may include a base plate 60 having a pad 62 attached thereto and a threaded member 64 extending laterally therefrom, wherein a knob 48 is attached to the member 64 such that rotation of the knob 48 causes the pad 62 to advance or retract, thus forming the force producing device 52. The force producing device 52 may also be any device known in the art for applying desired force or pressure such as, but not limited to, a spring-loaded type device, a plunger-type device with a stop or a tension band. A dial gauge G as shown in FIG. 10, which can be a digital (e.g., LED display) or an analog display, may also be attached to the force producing device 52 to indicate the pressure being applied. It is advantageous that the gauge G is of a type known in the art, such as a drag-type pointer, i.e., a pointer which remains in an indicating position even after the pressure has been removed so that the indicated value remains visible. Such pointers are readily released by, for example, depressing a button. Alternatively, an indicator light may also be used to indicate when the desired pressure is applied. Each of these positioning structures S can be located at various positions on the sectional board 12 depending on the body size of the patient's leg. Further, not all of the above-described positioning structures S need to be used during a radiographic procedure. For example, three positioning structures S may be used such as a foot support 44, a force producing device 52 and a pad 40 opposite the force producing device 52 so long as these structures S can hold the patient's leg and place adequate stress on the knee joint being X-rayed.

Additional positioning structures S may be used at various positions on the board 12 in order for a physician to apply stress on the leg at one or more desired locations. For example, either one or more force producing devices 52 or other positioning structures S may be used to apply a varus, valgus, anterior, or posterior directed pressure to the knee or other joint of a patient during a radiographic procedure. Each of the positioning structures S, including the holding members 16 and sectional board 12, can be coated with a bactericidal material, such as a Microban coated vinyl, for hygienic purposes.

In operation as shown in FIG. 9, a patient's leg is placed into the device 10 so that the knee region is supported by the foot support 44 which affixes the foot due to the engagement of the foot with the foot support 44. The back of the knee is placed on the angled pad 46 and the thigh and ankles are supported on one side by the stabilizing pads 40, 40', respectively. Pressure is exerted on the knee joint by the force producing device 52 wherein the leg is stabilized in its desired position. The leg and foot can be held in any necessary position because of the ability to add additional board sections and the ability to place any positioning structure S at any location on the sectional board 12.

FIG. 11 shows a second embodiment of a device 10' for applying stress to a knee that is somewhat similar to device 10 except for the differences noted below. Like reference numerals are used for like parts. The device 10' includes a base board 70 having a plurality of slots 72 therein, adjustable holding members 16' for engagement with the slots 72 and positioning structures S' supported on the holding members 16'. The holding members 16' may be of any type known in the art, such as a nut and bolt arrangement or clamp arrangement, so long as the holding member 16' can be slidably moved along the slot axis thereby providing the capability to adjust or move the positioning structures S' to a desired position on the base board 70. The positioning structure S' of device 10' may include a foot support 44', a force producing device 52' and a ruler 74 for measuring the position of a patient's leg. Here, the foot support 44' uses a boot that can support both the foot and ankle thus eliminating the stabilizing pads 40, 40' as in device 10. Further, the force producing device 52' is similar to the force producing device 52 and includes a support frame 42', a pad 62' attached to a member 64' extending laterally therefrom, wherein a knob 48' is attached to the member 64' for advancing and retracting the pad. The positioning structure S' as shown in FIG. 11 may be used interchangeably with the corresponding positioning structure S shown in FIGS. 5-10. Adapting the holding members 16 and 16' to support any of the positioning structures S and S' is also well known in the art.

While specific embodiments of the invention have been described in detail, it will be appreciated by those skilled in the art that various modifications and alternatives to those details could be developed in light of the overall teachings of the disclosure. The presently preferred embodiments described herein are meant to be illustrative only and not limiting as to the scope of the invention which is to be given the full breadth of the intended claims and any and all equivalents thereof.

The invention claimed is:

1. A knee positioning device for applying stress to a knee joint during a radiographic procedure, the device comprising:
   a plurality of planar sectional support boards having a plurality of spaced apart slots therein, wherein each board is linearly and releasably attached directly to each other; and
   a plurality of holding members positioned within the slots, wherein each holding member supports a positioning structure, the positioning structure comprises a foot support positioned at an end of the board for supporting a user's leg, a stabilizing member positioned upstream of the foot support for supporting one side of the leg and a force producing member positioned opposite of the stabilizing member for applying pressure to an opposite side of the leg.

2. The knee positioning device of claim 1, wherein the holding member comprises a first section, a second section and a flange section defined therebetween, wherein the first section is inserted into the slot and the flange abuts against the board such that the second section extends therefrom.

3. The knee positioning device of claim 1, wherein the slots defined in the board comprise circular bore holes extending therethrough.

4. The knee positioning device of claim 1, wherein the slots defined in the board are elongated such that the holding members are slidably moved along a longitudinal axis of the slots.

5. The knee positioning device of claim 1, wherein the positioning structure further comprises an angled knee pad and a femoral and/or tibial stabilizing pad.

6. The knee positioning device of claim 1, wherein the positioning structure comprises an opening therein for receiving the second section of the holding member such that the positioning structure is releasably attached to the sectional board.

7. The knee positioning device of claim 1, wherein each of the plurality of sectional boards is slidably attached to each other.

8. The knee positioning device of claim 1, wherein the sectional boards are rectangular shaped.

9. A knee positioning device for applying stress to a knee joint during a radiographic procedure, the device comprising:
 a plurality of planar sectional support boards having a plurality of spaced apart longitudinal slots therein, wherein each board is linearly and releasably attached directly to each other; and
 a plurality of holding members positioned within the slots, wherein each holding member supports a positioning structure, the positioning structure comprises a foot support positioned at an end of the board for supporting a user's leg, a stabilizing member positioned upstream of the foot support for supporting one side of the leg and a force producing member positioned opposite of the stabilizing member for applying pressure to an opposite side of the leg.

10. A method of performing a radiographic procedure of a patient's leg, the method comprising:
 providing a knee positioning device comprising at least two planar sectional support boards having a plurality of spaced apart slots therein and at least three holding members positioned within the slots, wherein each holding member is configured to support a positioning structure;
 releasably and linearly attaching the support boards directly to each other;
 attaching the positioning structure to the support boards via the holding members;
 placing a patient's leg on the support boards; and
 adjusting the positioning structures such that pressure is applied to a knee joint of the patient's leg.

* * * * *